US00PP11965P2

(12) United States Plant Patent
van Veen

(10) Patent No.: US PP11,965 P2
(45) Date of Patent: Jun. 26, 2001

(54) ASTILBE PLANT NAMED 'VISION IN RED'

(75) Inventor: Wim van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,563

(22) Filed: Dec. 29, 1999

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Astilbe plant named 'Vision in Red', characterized by its upright plant habit; rapid growth rate; dark green leaves; dark purple stems and petioles; very freely and uniformly flowering; strong flowering stems; and attractive purple-colored flowers.

2 Drawing Sheets

BACKGROUND OF THE INVENTION

The present invention relates to a new and distinct cultivar of Astilbe plant, botanically known as *Astilbe chinensis*, and hereinafter referred to by the cultivar name 'Vision in Red'.

The new cultivar is a product of a planned breeding program conducted by the Inventor in Noorden, The Netherlands. The objective of the breeding program was to develop new Astilbe cultivars with purple-colored flowers.

The new cultivar originated from a cross made by the Inventor in 1993 of the *Astilbe chinensis* cultivar 'Pumila', not patented, as the male or pollen parent, with the *Astilbe chinensis* cultivar 'Purpurkerze', not patented, as the female or seed parent.

The cultivar 'Vision in Red' was discovered and selected by the Inventor as a flowering plant within the progeny of the stated cross in a controlled environment in Noorden, The Netherlands.

Asexual propagation of the new cultivar by divisions harvested at Noorden, The Netherlands, has shown that the unique features of this new Astilbe are stable and reproduced true to type in successive generations.

SUMMARY OF THE INVENTION

Plants of the cultivar 'Vision in Red' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Vision in Red'. These characteristics in combination distinguish 'Vision in Red' as a new and distinct cultivar:

1. Upright plant habit.
2. Rapid growth rate.
3. Dark green leaves.
4. Dark purple stems and petioles.
5. Very freely and uniformly flowering.
6. Strong stems.
7. Attractive purple-colored flowers.

Plants of the new Astilbe differ from plants of the male parent, the cultivar 'Pumila', in leaf color, in addition, plants of the new Astilbe are have shorter and stronger (thicker) flowering stems than plants of the cultivar 'Pumila'.

Plants of the new Astilbe are more compact, narrower and faster-growing than plants of the female parent, the cultivar 'Purpurkerze'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Astilbe.

The photograph on the first sheet comprises a side perspective view of a typical plant of the new Astilbe.

The photograph at the top of the second sheet comprises a close-up view of a typical inflorescence of the new Astilbe.

The photograph at the bottom of the second sheet comprises a close-up view of a typical leaf of the new Astilbe.

DETAILED BOTANICAL DESCRIPTION

In the following description, color references are made to The Royal Horticultural Society Colour Chart except where general terms of ordinary dictionary significance are used. Plants used for the description were about one year-old and grown in 17-cm containers under outdoor production conditions which closely approximate commerical production conditions during the spring and summer in Noorden, The Netherlands.

Botanical classification: *Astilbe chinensis* cultivar 'Vision in Red'.

Parentage:

*Female parent.*—*Astilbe chinensis* cultivar 'Purpurkerze', not patented.

*Male parent.*—*Astilbe chinensis* cultivar 'Pumila', not patented.

Propagation:

*Type.*—By root divisions.

*Time to rooting.*—About 3 months at temperatures about 18° C.

*Root description.*—Fine.

Plant description:

*Crop time.*—From divisions, about 40 weeks are required to produce fully-grown flowering plants in 17-cm containers.

*Form.*—Upright; inverted triangle.

*Branching habit.*—Flowering stems and leaves arise from the roots.

*Plant height.*—About 70 cm.

*Area of spread.*—About 65 cm.

*Vigor.*—Moderate; rapid growth rate.

*Stems.*—Length: About 70 cm. Internode length: About 14 cm. Texture: Many soft, light gray hairs, about 2 mm in length. Color: 183A.

*Foliage description.*—Arrangement: Bi-ternately compound; alternate. Quantity of leaflets per leaf: Typically about 40 to 50. Leaf length, including petiole: Up to about 50 cm. Leaf width: About 40 cm. Leaflet length: About 5 cm. Leaflet width: About 3 cm. Leaflet shape: Ovate to elliptic. Leaflet apex: Acute to apiculate. Leaflet base: Attenuate. Leaflet margin: Doubly serrate. Leaflet texture: Lower surface slightly lustrous; both surfaces with short stiff hairs along the veins, light gray, about 1 mm in length. Leaflet color: Young foliage, upper surface: 135A. Young foliage, lower surface: 137B to 137C. Mature foliage, upper surface: 139A. Mature foliage, lower surface: 137B to 137C. Venation, upper surface: 137A. Venation, lower surface: 139D. Petiole: Length: About 23 cm. Diameter: About 2.5 mm. Texture: Soft light gray hairs, about 1.5 mm in length. Color: 183A.

Flower description:

*Flower type and habit.*—Numerous small single flowers arranged in branched panicles. Very freely flowering with about 7,000 flowers and flower buds per plant. Flowers sessile.

*Natural flowering season.*—Continuously flowering typically during the summer.

*Flower longevity.*—Flowers last a few weeks on the plant and more than one week as a cut flower. Flowers persistent.

*Fragrance.*—Sweet, pleasant.

*Flower buds.*—Length: About 2 mm. Diameter: About 1.7 mm. Shape: Ovate to orbicular. Rate of opening: About two to three weeks from visible bud to fully opened flower. Color: 70B to 74B to 74C.

*Flower size.*—Length (height): About 3 mm. Diameter: About 2 mm.

*Petals.*—Arangement: Five. Shape: Ligulate to linear. Apex: Acute. Margin: Entire. Length: Less than 3 mm. Width: About 0.5 mm. Texture: Smooth. Color: When opening, upper and lower surfaces: 77A. Fully opened flower, upper and lower surfaces: 77A, becoming darker than 77A to 79A.

*Calyx.*—Length: About 2.75 mm. Width: About 3 mm. Number of sepals: About five. Sepal shape: Ovate Sepal apex: Obtuse. Sepal margin: Entire. Sepal color (Both surfaces): Close to 74C to 74D.

*Reproductive organs.*—Stamens: Stamen number: About ten. Anther attachment: Basifixed. Anther length: Less than 0.5 mm. Anther color: Pale purple-gray. Pollen amount: Scarce. Pollen color: Pale purple-gray. Pistils: Pistil number: Two. Pistil length: About 2 mm. Stigma shape: Club-shaped. Stigma color: Close to 67A. Style length: About 1.5 mm. Style color: 67A. Ovary color: 67A.

*Seed.*—Length: Less than 0.5 mm. Diameter: Less than 0.5 mm. Color: Light brown.

Disease resistance: Under commercial conditions, plants of the new Astilbe are slightly susceptible to diseases common to Astilbe.

It is claimed:

1. A new and distinct cultivar of Astilbe plant named 'Vision in Red', as illustrated and described.

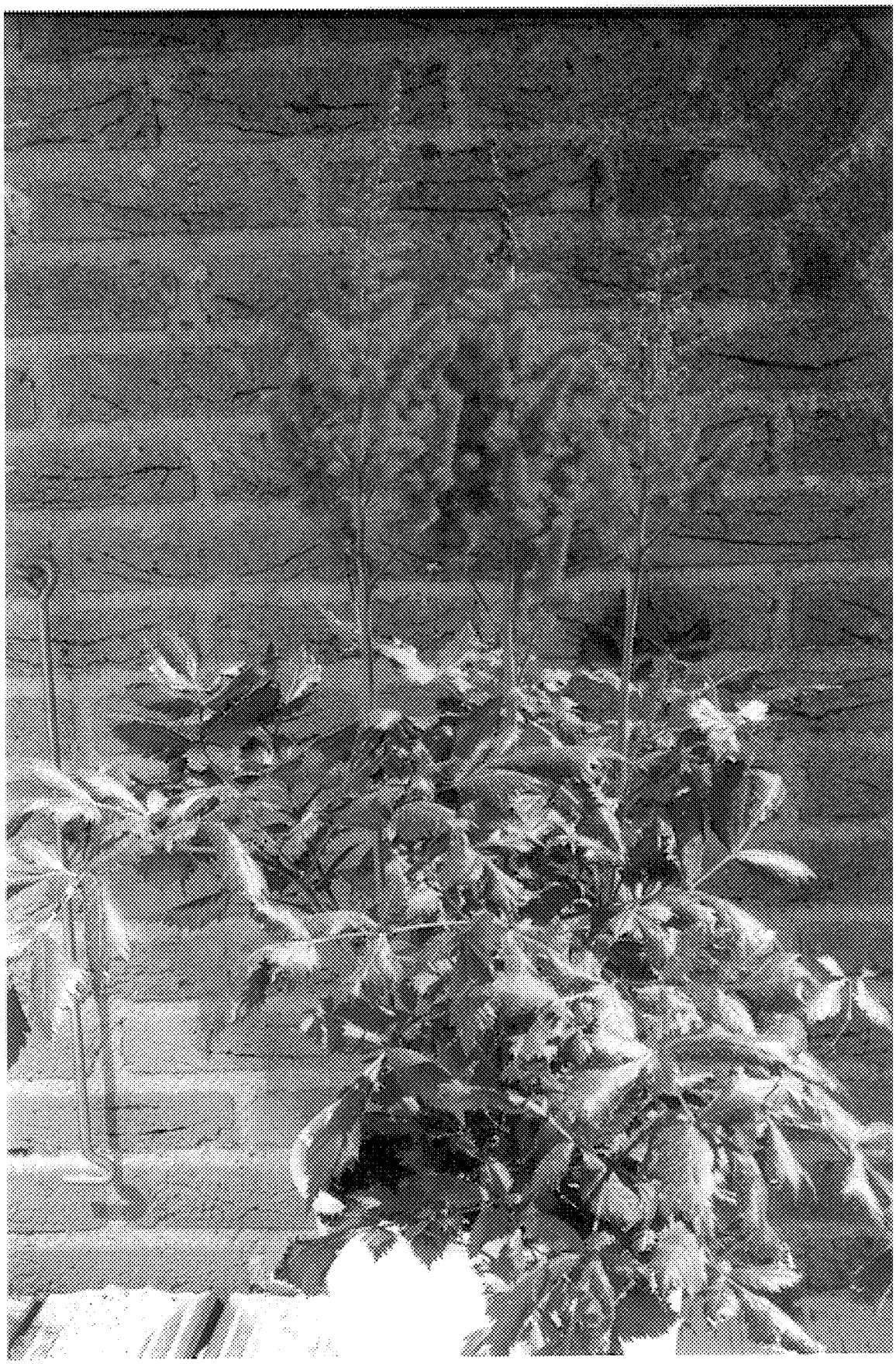

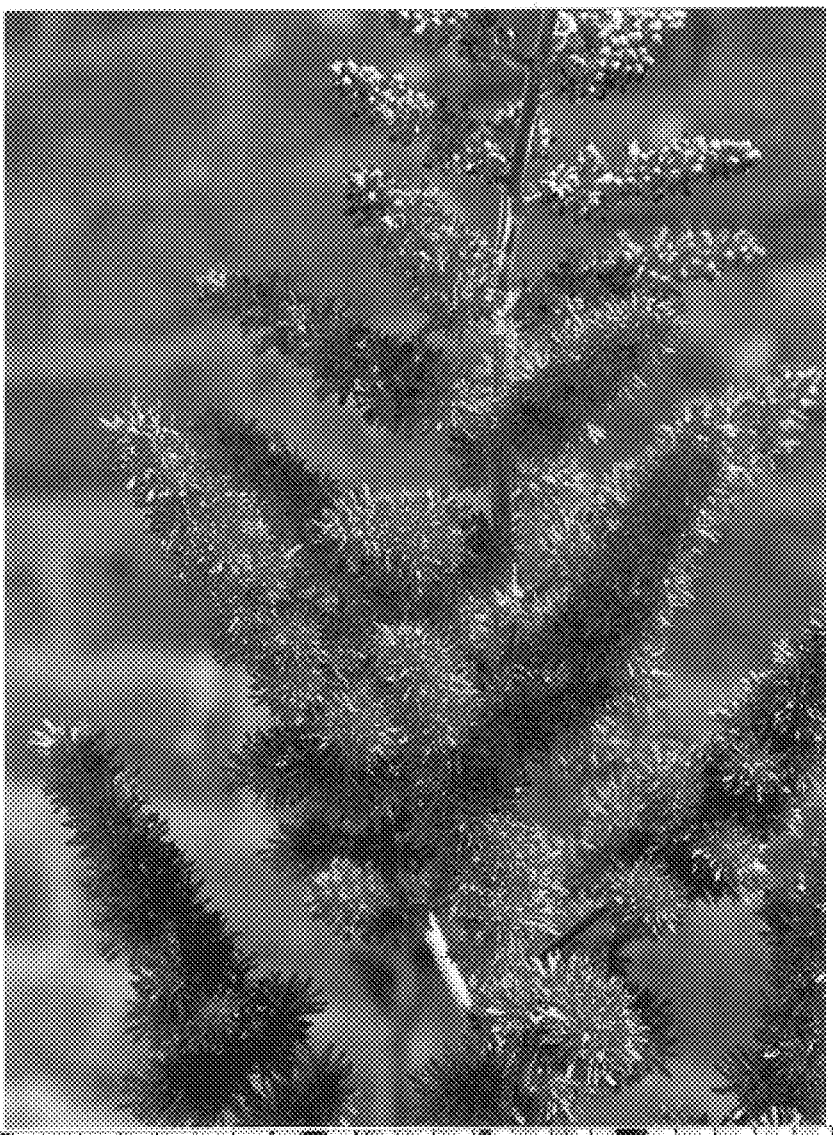
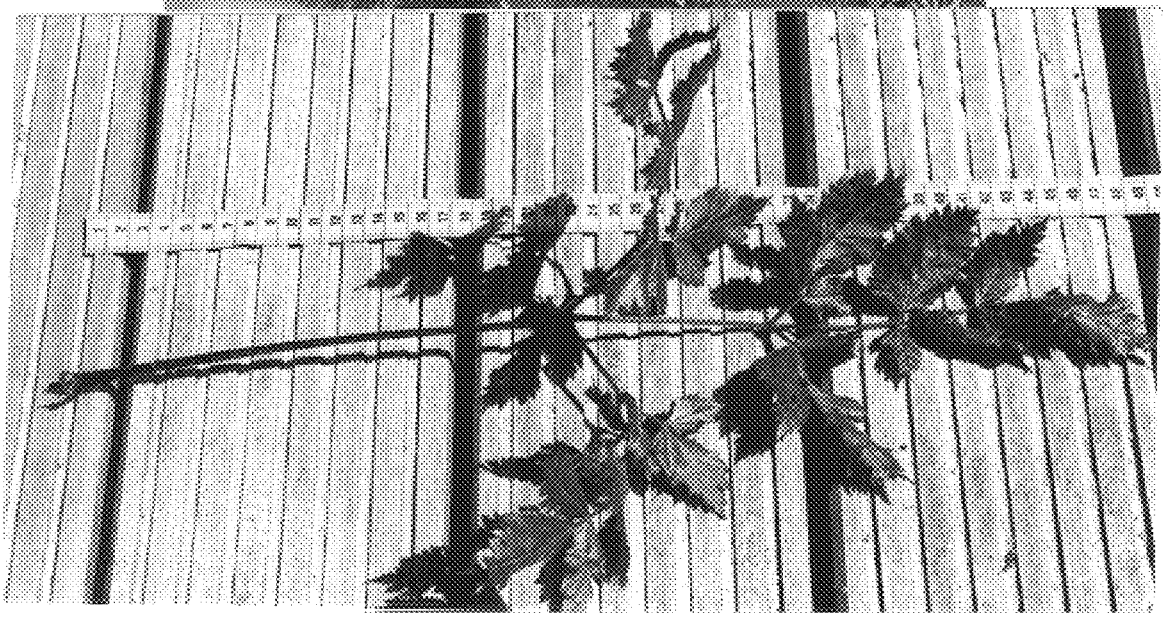

* * * * *